United States Patent [19]

Katz et al.

[11] 4,345,900
[45] Aug. 24, 1982

[54] DENTURE MEANS AND METHOD

[76] Inventors: Harry S. Katz, 785 Pleasant Valley Way, West Orange, N.J. 07052; Sidney Schneider, 576 Sussex Ave., Morristown, N.J. 07960

[21] Appl. No.: 573,324

[22] Filed: Apr. 30, 1975

Related U.S. Application Data

[63] Continuation of Ser. No. 398,936, Sep. 20, 1973, abandoned, and a continuation-in-part of Ser. No. 241,706, Apr. 6, 1972, abandoned.

[51] Int. Cl.² ............................................. A61C 13/22
[52] U.S. Cl. .................................................. 433/171
[58] Field of Search ................. 425/388, DIG. 11; 264/16, 17, 18; 32/2

[56] References Cited

U.S. PATENT DOCUMENTS

| | | | |
|---|---|---|---|
| 2,341,155 | 2/1944 | Myerson | 32/17 |
| 3,241,238 | 3/1966 | Kersten | 32/2 |
| 3,460,252 | 8/1969 | Schneider et al. | 32/17 |
| 3,474,497 | 10/1969 | Watts | 425/388 |

FOREIGN PATENT DOCUMENTS 1085599  10/1967  United Kingdom ............... 32/2

Primary Examiner—Robert Peshock
Attorney, Agent, or Firm—Michael J. Ram

[57] ABSTRACT

Disclosed are devices and methods for forming a denture in a tray either in-situ in the mouth of a dental patient or against a model of the gums. A tray which is adapted to hold false teeth and which formable is fitted or conformed to the gums of the patient, or to an impression of the gums of the patient, while employing a spacer to separate said formable tray and gums or impression of the gums, said spacer having a thickness representing approximately the thickness of the denture-forming plastic material desired in the denture. The resulting conformed tray with the spacer separated provides a former into which liquid curable denture-forming material is then placed. The resulting assembly can then be inserted into the mouth where pressure is applied and the denture-forming material cures to form the denture which is thereafter separated from the former.

76 Claims, 16 Drawing Figures

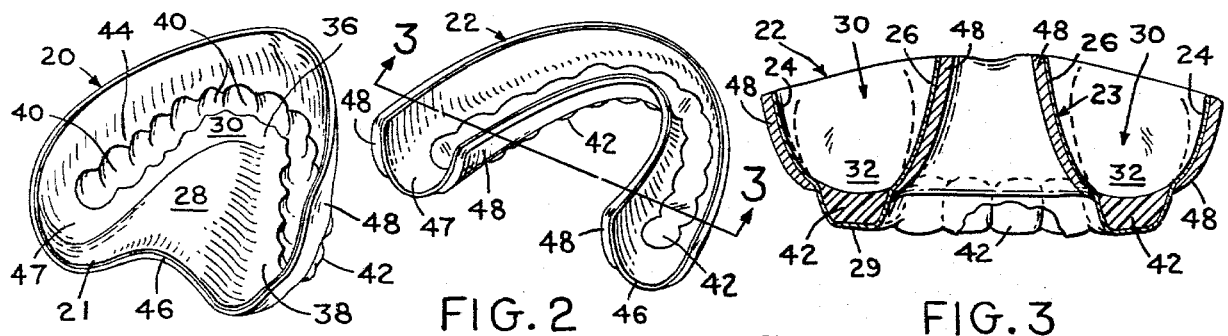

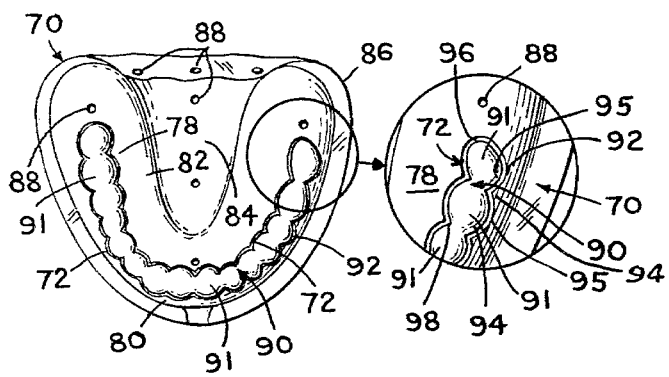
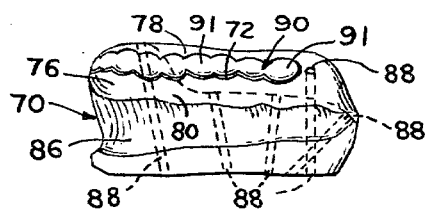
FIG. 10
FIG. 9
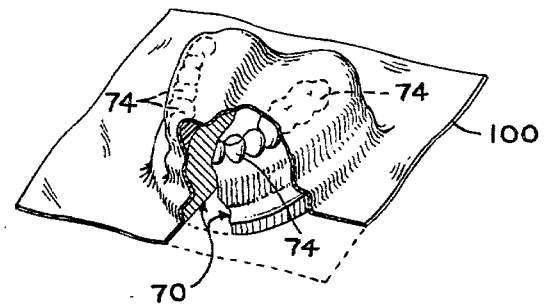
FIG. 11
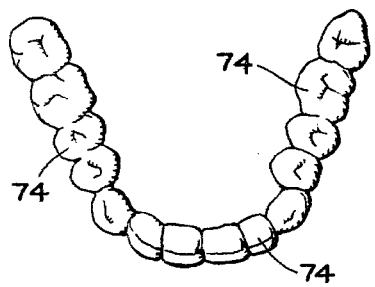
FIG. 12
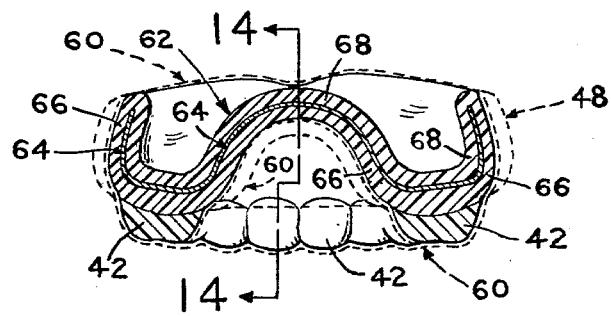
FIG. 13
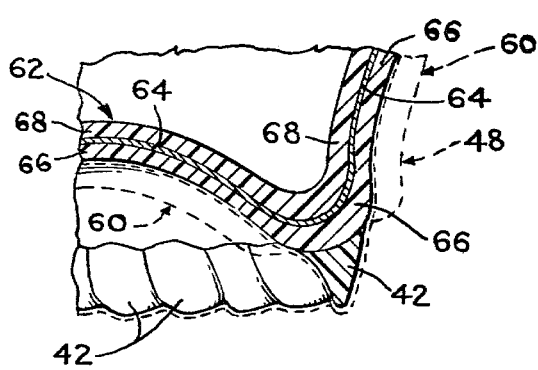
FIG. 14

DENTURE MEANS AND METHOD

This is a continuation of application Ser. No. 398,936 filed Sept. 20, 1973 and now abandoned and a continuation-in-part of application Ser. No. 241,706, filed Apr. 6, 1972 and now abandoned.

In U.S. Pat. No. 3,460,252 there is described various means and methods for forming a denture in-situ in the mouth of a dental patient. In U.S. Pat. No. 3,621,575 there is described various improvements in or relating to in-situ dentures involving the use of a gutter shim or shims having a gutter portion and/or different curable denture-forming materials. In our copending application, Ser. No. 126,507, filed Mar. 22, 1971, there are described means and methods for making an in-situ denture involving the use of a former or adapted tray comprising a tray and impression material in which there has been formed a general impression of the patient's gums by the taking of a general impression of the gums through a spacer in a tray holding false teeth and having impression material therein.

An object of the present invention is to provide improvements in the formation of dentures, including particularly the in-situ formation of dentures.

Another object is to provide new and improved devices for use in the formation of dentures.

Another object is to provide new and improved methods for the formation of dentures.

A further object is to provide novel and efficient means for making a tray for use in the formation of dentures.

A still further object is to provide improved and more efficient procedures for in-situ denture formation of dentures.

These and other objects of the present invention will be evident from the following description of the invention and accompanying drawings in which:

FIG. 1 is a perspective view showing a formable upper tray without teeth therein.

FIG. 2 is a perspective view showing a formable lower tray with teeth therein.

FIG. 3 is a section taken along line 3—3 of FIG. 2 with dotted lines illustrating the changed outline of the section after conforming of the tray.

FIG. 4 is a top view showing a formable upper tray having a set of pre-cast false teeth therein.

FIG. 5 is a view showing a tray in elevation and in section taken along line 5—5 of FIG. 4 with dotted lines illustrating the changed outline of the section after conforming of the tray.

FIG. 6 is an exploded view illustrating the formation of a conformed upper tray and showing a model of the gums of patient, a shaped spacer which is placed over said model and a formable tray placed over said spacer.

FIG. 7 is a perspective view showing a shaped spacer for use in forming a conformed lower tray.

FIG. 8 is a perspective view illustrating the forming of a conformed upper tray.

FIG. 9 is a top view of a die block for use in forming a basic tray.

FIG. 10 is a side elevation view of the die block shown in FIG. 9.

FIG. 11 is a perspective view partly broken away illustrating a plastic sheet vacuum formed over a die block with false teeth thereon.

FIG. 12 is a top view of a pre-cast set of false teeth.

FIG. 13 is a representative vertical section presented as if taken laterally through a finished denture while still within a conformed tray at a point similar to the section of FIG. 5.

FIG. 14 is a representative vertical section presented as if taken longitudinally through the center of a finished denture while still within a conformed tray.

GENERAL METHOD OF MAKING CONFORMED TRAY OR FORMER

Figure 15:
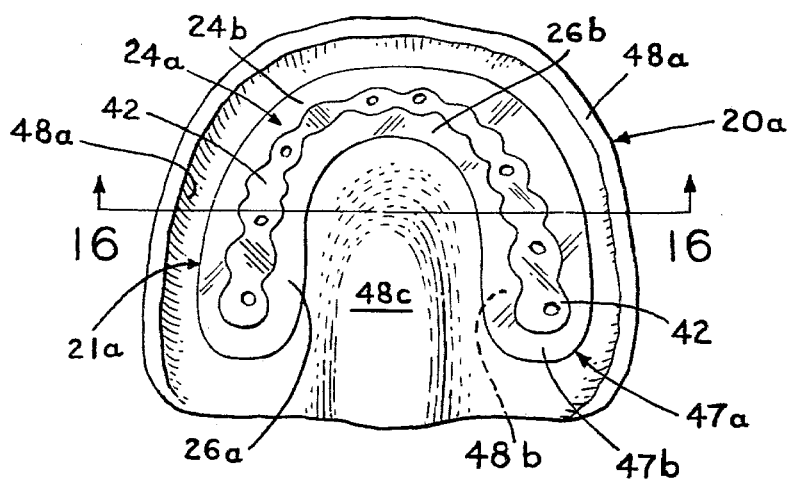
FIG. 15 is a top view showing another detailed embodiment of a formable upper tray having a set of pre-cast false teeth therein.

In accordance with the present invention, a tray which holds or is adapted to hold false teeth and which is formable is pressed against a spacer which by its thickness controls the thickness of the denture-forming plastic material desired in the denture and while said spacer is in contact with the gums of the patient including the palate in the case of an upper denture, or with an impression of the gums of the patient including the palate portion in the case of an upper denture, to form a tray conformed to the gums of the patient including the palate in the case of an upper denture and differing spatially from said gums including the palate in the case of an upper denture by approximately the desired thickness of denture-forming plastic as determined by the spacer during such conforming of the tray to such gums with the spacer there-between. The resulting conformed tray or former is then used in the making of a denture as described for example, in U.S. Pat. No. 3,621,575.

Characteristics of Formable Tray and Definitions in Relation Thereto

The formable trays contemplated by or for use in the present invention may be suitably embodied in any one of several ways and may be, for example, formable at room temperature of formable at elevated temperature, i.e. heat formable. As used herein the term "formable" shall mean formable or shapeable at either about room temperature or at elevated temperatures while the term "deformable" shall mean formable or shapeable only at temperatures above room temperature (ca. 70° F.), i.e. "deformable" means heat formable. The terms "formable," "shapeable" and the like as used herein indicate the ability to be changed from one set or rest position to another set or rest position by reason of the formable material itself, although it will be understood that materials and structures referred to as formable and the like may nevertheless be also flexible in either rest position. As generally used herein, the term "tray" usually contemplates essentially a complete device or assembly in which a denture may be formed; the term "basic tray" contemplates less than a complete tray but one holding or adapted to hold false teeth; the term "wall" which usually is associated with a complete "tray" contemplates an essentially complete or full wall of a tray (or denture) to the extent necessary to define one side of the whole of a gum-receiving portion and optionally or to the extent necessary may extend to of form a side for holding false teeth, and accordingly consists of a single material or, as in the case of the specific preferred embodiments of the formable tray herein disclosed, more than one material; the term "wall portion" contemplates less than the whole of or any part or portion of a complete or full "wall" independent of the height of the wall portion; the terms "trough" and "channel" contemplate or visualize an area defined between adjacent walls or wall portions and is open at the top but optionally open or closed at the bottom by a bottom portion; the term "flange" contemplates a short or abbreviated wall portion with the outer flange extending outwardly from approximately the level of the tops of the false teeth at their individual points of maximum outside width to a height which is no more than 70% of the distance, i.e. vertical cross-sectional surface travel, along the outer tray wall defining the gum-receiving portion, usually between 10% and 50%, and, in the case of an inner flange, a distance to a height no greater than the maximum height attainable by the outer flange, and wall portions meeting such limitation with respect to at least 50% of its length along the arch is defined as a "flange."

First Embodiment of Formable Tray

A generally preferred type formable tray in accordance with the invention is shown in FIGS. 1–5, and FIGS. 1, 4 and 5 show a formable tray 20 for making an upper denture. The formable tray 20 includes a basic tray 21 which has the general shape or outline of the arch of the mouth and comprises an outer uprising flexible wall portion 24 and a palate portion 28. While the inner flexible wall portion 26 is referred to as an "uprising" wall, it will be noted that portions or all of this wall portion above the teeth may be only slightly uprising or even horizontal in the tray prior to conforming to permit the palate to be raised a fairly substantial amount during the conforming. The inner and outer wall portions are suitably interconnected along the integral bottom portion 29. The basic tray 21 is preferably formed of a thin flexible plastic material which desirably has little elastic memory. The preferred plastic materials are polymeric materials having a Vicat softening point (ASTM D-1525) in the range of 100° F. to not excess to 160° F., preferably 120° F. to 140° F. and stiffness (ASTM D-747) in the range of 500 p.s.i. to not in excess of about 9,000 p.s.i., preferably between about 1,000 p.s.i. to about 4,000 p.s.i. Suitable polymeric material having such properties may be readily obtained, for example, in copolymers of ethylene and vinyl acetate containing 65% to 88% ethylene and 12% to 35% vinyl acetate, preferably 67% to 80% ethylene and 20% to 33% vinyl/acetate. A particularly preferred ethylene-/vinyl acetate copolymer containing about 72% ethylene and 28% vinyl acetate and having a Vicat softening point of about 125° F. and stiffness of about 1,700 p.s.i. may be obtained under the trade mark and identification "ALATHON" EVA 3175 or 3170. The thickness of the outer wall portion of the basic tray is preferably in the range of 3 to 12 mils, more preferably 4 to 8 mils, although the thickness of the palate portion will be less when the tray is produced by vacuum forming.

The tray is preferably prepared by vacuum forming from a sheet of material, although other known methods such an injection and blow molding can be used.

The outer wall portion 24 and inner wall portion 26 together with bottom portion 29 can be taken collectively as forming a trough 30 of which the upper portion is a gum-receiving portion 32 designed to receive a patient's gums and of which the lower portion is designed to receive false teeth, the gum-receiving portion having a bottom defined by and including the exposed top surface of the false teeth which are to be subsequently joined to denture-forming material. The trough 30 including the lower portion thereof is relatively narrow at the forward position 36 of the tray and gradually increases in width along the side portion 38 of the tray as shown particularly in FIG. 4, and such construction may be utilized to contribute to the snug holding of the teeth in the tray.

Impressed within said lower portion of the trough 30 of the basic tray 21, as during molding or by any other suitable method of indicating, are indicia or cavities 40 preferably in the form of spaced or successive depressed pocket portions 40 which desirably are openly interconnected continuously along the arch of the lower portion of the trough. The indicia or pocket portions 40 hold and/or indicate the placement of the false teeth 42 within the basic tray 21 prior to making the dentures. Each tooth is thus snugly held within a depression or pocket 40 and the teeth 42 are further held because the trough 30 increases gradually in width. The teeth 42 can therefore be supported and cannot readily move out of place without the aid of an adhesive although an adhesive is employed in the preferred embodiments of the invention. The false teeth employed in the invention and disposed within the depressed portions 40 may be provided as a single case unit containing all necessary teeth as shown in the drawings, or may be provided by a plurality of teeth sections containing one or more teeth, or may all be provided as individual teeth which may or may not be held by a binder material such as silicone rubber, as described in U.S. Pat. Nos. 3,460,252 and 3,621,575. Small holes (FIG. 15) may be drilled or molded into the center top of each of the teeth to promote the strength of the bond between the teeth and denture-forming material.

Both the upper basic tray 21 and lower basic tray 23 desirably have a small outward step 44 which is more pronounced towards the rear of the tray than the front, and which may be more pronounced with respect to the outer walls 24 than the inner walls 26. The steps 44 allow for the natural stepping out of the gums from the teeth. When false teeth are to be positioned in the cavities 40 without being imbedded in a binder, then it will be evident that the step 44 will be further more pronounced to account for the natural stepping out of the gums from the teeth, as shown for example in FIGS. 3 and 5. The trough 30 can be said to terminate at the back of the tray and the portion of the trough 30 between the last tooth on each side and the rearward edge 46 may be called the platform trough 47. The rearward edge 46 can be said to extend across the rearward edge of the palate and the entire length of such rearward edge 46 is preferably turned up slightly to facilitate in controlling the flow of excess denture material out of the tray during the denture-forming operation.

The formable tray 20 has secured to the outside surface of the basic tray 21 a formable material 48 which can be formed or shaped and thus effect a repositioning and/or reshaping of outer uprising flexible wall portion 24, the inner uprising flexible wall portion 26 and palate portion 28 because said wall portions and palate portion are secured to the forming material 48 and are composed of a material of sufficiently low memory that such walls and palate retain the new shape and/or position. Hence, the basic tray is preferably composed of a material which is flexible and shapeable and capable of being held in a new position but such material is not itself formable as the term is used herein. As shown particularly in FIGS. 1–5, the formable material covers virtually all of the outside surfaces of the basic tray 21, except for the teeth or at least excepting the lower parts of the teeth, but including preferably the outside surface of the platform trough 47. It is also generally possible that the upper region of the outer uprising wall portion 24 (and also the inner wall portion in the case of a lower tray) be left uncovered by the forming material to facilitate trimming thereof in the preliminary fitting of the tray, and such omission is permissible because the precise forming or adapting of such upper region of the tray is less important in accomplishing the objectives of the invention. When left uncovered such upper region of the basic tray 21 can be made more rigid or have a greater memory as by, for example, reinforcing with a thin strip of stiffer plastic material, as the general position or orientation of such upper region can be satisfactorily set by the shaping of the forming material secured to the balance of the uprising walls.

The forming material 48 itself may be any of several suitable materials including room temperature formable materials including metals such as lead and aluminum and deformable materials such as plastic compositions and the like including waxes. A preferred material is one which is deformable and also flowable or spreadable at the deformation temperatures, and such a preferred material is a wax well known in the dental art as "boxing wax." Such wax is readily formable and spreadable at only moderately elevated temperatures of about 110° F. to 170° F. yet it has fairly good shape-retaining properties at and below room temperature. An example of a preferred wax is a microcrystalline petroleum derivative having a softening point in the range of 140° F. to 170° F. The use of formable material which is flowable and thus can be spread or compacted is helpful in reducing the number of different upper trays which must be made available to fit different patients. Other materials demonstrating considerable potential for use as a formable material include standard and commercially available base plate materials comprising shellac, gutta percha and fillers such as mica and silica but which has been modified by the addition of quantities of shellac to bring the softening point to within the range of preferably from 140° F. to 145° F. A suitable mold release material such as silicone may be sprayed or otherwise deposited on such modified base plate material to facilitate separation of the tray from any surfaces of the cured denture-forming material in which it is in contact. Other such formable materials include those which may be prepared from transpolyisoprene such as that obtained under the Trademark "TRANSPIP" from Polysar Ltd. of Sarnia, Ontario, Canada, by modifying the same with filler material such as dynel flock to increase rigidity as desired and with a wax such as carnauba wax, the preferred boxing was indicated above or paraffin wax to obtain the desired softening point which is preferably in the range of from 140° F. to 170° F. Such modified transpolyisoprene material may also have incorporated therein zinc stearate, a powder of an ethylene/vinyl acetate copolymer such as the preferred copolymer material described herein or other suitable material as desired to impart a mold release capability to such material with respect to cured denture-forming material. Such modified base plate and modified transpolyisoprene materials also offer the advantages of not only being heat formable but also of being spreadable at deformation temperatures, i.e., capable of being worked or spread to cover in the final rest position a greater surface area that that covered during the original rest position and also capable of being worked or compacted to cover in the final rest position a lesser surface area should such a result be desired. The term "spreadable" as used herein is intended to indicate such formable material which can be spread or compacted to cover a greater or lesser surface area in the final rest position. In this connection, it can be appreciated that the palate area is subject to fairly wide variations among different patients yet the palate portion of the tray is relatively confined one in the sense that it may not be always possible to conform the palate portion of the basic tray to the palate of every patient, especially those having the higher palates, simply by conforming the formable material. The problem, therefore, when it exists, is one of total surface area of the palate of the patient as redefined by the spacer to be used versus the total surface area of the palate portion of the average basic tray to be used in practice. Accordingly, it is a preferred embodiment of the invention to use a formable, preferably deformable, material which can be spread, in conjunction with an upper tray in which at least the palate portion of the basic tray can be spread or stretched to conform to the contours and surface area of the patient's palate ad redefined by the spacer. While these objectives, as a practical matter, are now more readily accomplished in accordance with the Second Preferred Embodiment of a Formable Tray as hereinafter described, such a formable tray may be constructed in accordance with the instant embodiment by employing a basic upper tray made from a sheet of suitable plastic material which is capable by reason of its thinness and/or otherwise of being stretched while at the same time the material has a sufficiently low elastic memory that it will not work against or force the conformed formable material from its conformed configuration. Suitable sheet materials found to give such desired results are those composed of more preferred ethylene/vinyl acetate copolymers (EVA) heretofore mentioned, which are rubbery type materials which can also be raised above their softening points at the same time that the deformable material is made formable by heating. It will be evident that equivalent conformed trays or formers may be provided by any of a variety of other means. For example, instead of making the former entirely from the preferred thin EVA sheet material, a basic tray may be prepared from a thicker sheet of EVA or other material having, for example, a thickness of 15 to 30 mils, and the palate portion thereof cut away and replaced with a palate portion of a very thin EVA sheet, said replacement palate portion being joined to the resulting tray by heat sealing, bonding and the like. Any ridge line created in the final denture by the junction of the palate and remainder of the basic tray may be readily removed by conventional finishing techniques, e.g. grinding and polishing.

The formable material 48 may be joined and held to the basic tray 21 by any of several suitable means including by the natural adhesion of the formable materials for the basic tray material or by means of a glue, adhesive or binding substance which is desirably not brittle and which therefore can be formed along with formable material.

While the invention has been hereinabove largely described with reference to an upper tray and FIGS. 1, 4 and 5, it will be evident that the lower formable tray 22 with its lower basic tray 23 shown in FIGS. 2 and 3 may be analogously constructed, and like part numbers in FIGS. 2 and 3 and FIGS. 1, 4 and 5 refer to similar or completely analogous parts and features.

The formable trays of the first preferred embodiment therefore may be said to generally comprise inner and outer tray walls forming a trough of which the upper portion thereof defines a gum-receiving portion and the lower portion defines an area adapted to hold false teeth, said tray walls comprising: (1) a basic tray having inner and outer wall portions also defining said trough and a bottom portion integral therewith; and (2) formable material secured essentially to the entirely (more or less) of each of the basic tray wall portions adjacent said gum-receiving portion (and to the basic tray wall portion adjacent the upper part of the lower teeth holding portion of the trough), the trays for an upper denture also comprising a basic tray palate portion integral with the basic tray inner wall portion and a formable material secured to said palate portion and integral with the formable material secured to the basic tray inner wall portion.

SECOND EMBODIMENT OF FORMABLE TRAY

Figure 16:
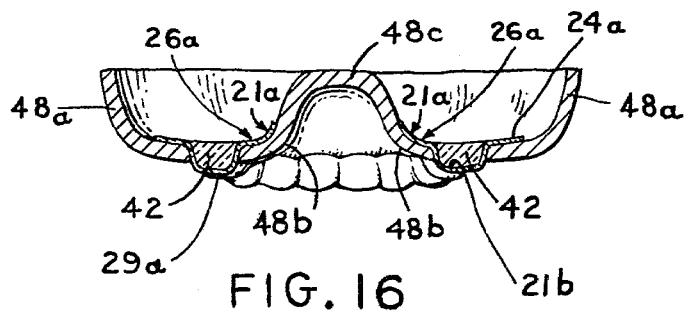
FIG. 16 is an elevational section taken along line 16—16 of FIG. 15.

Another preferred embodiment of a formable tray is illustrated in FIGS. 15 and 16 and it will be evident that one preferred method of preparing said formable tray involves simply the cutting, for example, with a razor blade, and removing from the formable tray of the First Preferred Embodiment most of the upper part of the outer wall portion 24 of the basic tray 21 and the entire basic tray palate and a substantial part of the upper part of the inner wall portion 26 of the basic tray 21. Thus, as shown in FIGS. 15 and 16, the formable tray 20a of the Second Preferred Embodiment includes an abbreviated basic tray 21a having the general shape or outline of the arch of the mouth and comprising an abbreviated outer flexible wall portion or outer flanged wall portion 24a having an outer flange 24b and an abbreviated inner flexible wall portion or inner flanged wall portion 26a having an inner flange 26b which are preferably joined together at rearward portion 47a having rearward flanges 47b. A basic tray bottom portion 29a is integral with the outer flanged wall portion 24a and inner flanged wall portion 26a. Outer formable wall portion 48a and inner formable wall portion 48b have their lower portions secured to the outside surface of the inner and outer basic tray wall portions 24a and 26a, particularly to the outer flange 24b and inner flange 26b, respectively, and a formable palate portion 48c is integral with the inner formable wall portion 48b. In this embodiment as shown in FIGS. 15 and 16, the abbreviated basic tray 21a is essentially a flanged or ⊔-shaped channel having the outline of an arch with the teeth 42 held in the channel body 21b. Such channel is well secured to the remaining formable portions of this formable tray and this may be accomplished in any of several ways. However, in the illustrated embodiment employing preferred materials the ethylene vinyl acetate copolymer channel is satisfactorily joined to the formable tray portions when made of boxing wax by natural forces such as natural adhesion, friction and the like. Thus, the natural adhesion between the underside surfaces of the inner and outer flanges 26b and 24b and the adjacent surfaces of formable wax of the formable inner and outer wall portions 48b and 48a provides adequate bonding in these areas. Also, since the formable material is in covering contact with upper side surfaces of the teeth holding channel and fills the indentations between teeth in this area, the combination of natural adhesiveness, friction and inherent wedge-like actions more than adequately secure the whole channel against movement in any direction relative to the formable portions of the tray.

In the formable tray 20a the thickness of wax-like formable materials is preferably greater than that contemplated for formable tray 20 and especially in areas not supported by corresponding portions of the basic tray, the wax thicknesses in the case of tray 20a being preferably from 0.08 inch to 0.15 inch while wax thicknesses in tray 20 are typically from 0.04 to 0.1.

The formable tray of the second preferred embodiment therefore may be said to generally comprise inner and outer tray walls defining a trough of which the upper portion thereof defines a gum-receiving portion and the lower portion defines an area adapted to hold false teeth, said tray walls comprising: 1) a basic tray in the form of a flanged channel in which the flanges define the lower portion of the gum-receiving portion and the channel defines said area adapted to hold teeth; and 2) formable material secured to said flanges; the trays for an upper denture also comprising a palate of formable material integral with the formable material secured to the inner flange.

It will be evident that a distinct advantage of formable tray 20a over tray 20 is that the absence of portions of the basic tray in key forming areas eliminates any resistance to forming which may be encountered by reason of such basic tray portions, and this is particularly desirable in the palate area where the most desired degree of forming may require a stretching of basic tray material. It will also be evident, because of particular concern directed to the palate area in this respect, that other modified trays 20, i.e. further preferred embodiments of a formable tray, can be contemplated in which the palate consists of a formable material while the outer tray wall has both formable material and the corresponding basic tray outer wall portion defining essentially the entirety of the gum-receiving portion; the inner basic tray wall portion, which is the less important of the three considerations in such case, being either of essentially full extension or height or in the form of a flange.

Other preferred formable trays for use in the present invention may be prepared from the stronger or normally more rigid formable materials, such as the modified base plate and modified transpolyisoprene materials above-described and comprise inner and outer formable walls defining a trough of which the upper part defines a gum-receiving portion and the lower part defines an area adapted to hold false teeth, the inner and outer formable walls being preferably connected by an integral bottom portion of the formable material and the trays for an upper denture having a formable plate integral with the inner wall. Such trays may be prepared in accordance with the method contemplated in our U.S. Pat. No. 3,460,252 by vacuum forming a sheet of the formable material over suitable die block or stone model of a denture to produce a tray having openly interconnected pockets, portions or cavities into which false teeth can be inserted. The insertion of the teeth, whether individually or in a set or sets, into such a tray is preferably accomplished by first warming the tray to or above its softening temperature in the pocket area and then inserting the teeth whereby the teeth will be more firmly held and the pocket area can be worked relative to teeth to more readily obtain the desired fitting of the teeth in the tray. In such trays it is also usually preferred to also lightly and temporarily bond the false teeth to the inside of the pockets area with a suitable adhesive such as that obtainable under the trade designation "Eastman 910". The adhesive can be suitably applied by painting it on the inside surfaces of the pocket area prior to inserting the teeth. Alternately, such formable trays may be prepared in accordance with the method hereinafter described with reference to FIGS. 9-11 whereby the formable material is vacuum formed over a die block on which a set of false teeth are removeably secured (and preferably painted with an adhesive) to obtain the formable tray with the false teeth securely held therein. The trays so produced may, however, be heated to raise the teeth-holding area to or above its softening point and worked to adjust the fitting of the false teeth therein as desired.

In all of the embodiments above described, it is possible, although less preferred, to remove the bottom portion of the basic tray, as by cutting, scoring and tearing and the like or otherwise provide such a structure, thereby physically exposing the bottoms of the false teeth, so long as the teeth are otherwise firmly held in the resulting bottomless channel as by friction and the wedge like action of formable material against the teeth and/or the use of a suitable adhesive removably securing the teeth to the channel walls, and the like.

The formable tray is used to obtain a former or conformed tray for use in making the final denture. The conformed tray may be very suitably prepared in either two general ways, i.e. by either conforming the tray to gums (and palate in the case of an upper denture) of the patient in situ in the mouth of the patient or by conforming the tray to a stone model of the gums (and palate in the case of an upper denture), said stone model being obtained in the usual way by taking an alginate impression of the gums (and any palate) followed by casting of the impression in stone. In either case, the formable tray is made into a former by the application of pressure to the formable parts of the formable tray while in position over the gums or model of the guns while the same are separated by the spacer. In the more preferred embodiments in which a deformable tray is used, the deformable tray, preferably with the false teeth already in position and carried thereby, is made formable by the suitable application of heat, for example, by immersing in hot water which is at a temperature at which the forming material attains its formable state, and which is also preferably at temperature high enough to raise the preferred basic tray plastic sheet material above its softening point, e.g. a water temperature of from 120° F. to 160° C. Immersion times are typically ½ to 4 minutes. As shown in a preferred embodiment which is illustrated in FIG. 6, the upper formable tray 20 with the forming material 48 in the formable state is then placed over a stone impression 50 of the gums 52 and palate 54 of the patient and is readied for the conformation thereto by providing a spacer 56 intermediate said tray and stone impression. The spacer 56 is then positioned in contact with the stone impression and the tray gently positioned on the assembly and pressed down carefully over the spacer and the stone impression so that the spacer adopts the configuration of the inside of the tray and is preferably evenly fitted thereto in the sense that the end edges of the spacer are about equidistant from the top of the walls of the tray, as illustrated in FIG. 8. Alternately, the spacer may be fitted inside the tray and this assembly position on the stone impression. In either case, the tray which is still in formable condition by virtue of the heating thereof, is then conformed to the gums and palate portion by the application of mild finger pressure to the formable material at appropriate locations as illustrated by the pressure arrows in FIG. 8. The tray thus processed conforms substantially to the gums and palate of the patient except that it differs therefrom spatially by the thickness of the spacer. The thus conformed tray is removed from the stone impression and cooled to a temperature at which the deformable material is no longer formable. Cooling may be accomplished simply by allowing the conformed tray to cool in the atmosphere to room temperatures but is preferably expedited by immersing the conformed tray in cold water for about ½ to 5 minutes. The spacer may be separated from the tray before or after cooling. Typical differences between the formable tray 20 and the conformed tray are illustrated in FIGS. 3 and 5 where the outline of the wall and palate portion of the conformed tray are shown by dotted lines, and such upper conformed tray is also shown in FIGS. 13 and 14.

The spacer employed in the present invention represents an important functional aspect thereof and is used in conjunction with the tray-conforming operation to control and determine approximately the thickness of the final denture.

Thus, the basic purpose of the spacer is to allow for and determine approximately the space to be later occupied by the denture-forming plastic material at least in the more critical areas which are adjacent the lower and middle regions of the inner wall 26 and the outer wall 24, and the palate in the case of an upper denture. The spacer may be of uniform thickness or it may be of non-uniform thickness to provide for areas in which it will be subsequently desired or required to have a lesser or greater thickness of the plastic denture material. In practice, very satisfactory results have been obtained employing a spacer of uniform thickness. The relationships between the thickness of the spacer and the thickness plastic denture material in the final denture is indicated as approximate. Since the later and final denture-forming step exerts some expansive pressure on the wall of the tray, especially when employing a shim, it will be evident that the spacer usually represents the minimum thickness of the denture. For example, when employing a spacer of uniform thickness and a shim, it has been found that the thickness of an upper denture in the areas adjacent the inner wall and most of the palate portion of the tray are about equal to or very slightly greater than the corresponding thickness of the spacer. The areas adjacent the outer wall of the tray (and the inner wall in the case of a lower denture) tend to be thicker than the spacer due to the flowing out of denture-forming material at these locations but such thickness can be controlled by the application of pressure to the tray during the forming process to squeeze out excess denture-forming plastic material, but in any event, the thickness of the spacer provides a very desirable control in arriving at a desirable thickness for such areas. However, the very front of the denture adjacent the front of the outer wall of the tray may be of a thickness about equal to or even somewhat less than that of the spacer (if the spacer is not made thinner in such area) because it is a part of the preferred technique in forming the denture to squeeze out an extra amount of denture-forming material to make this area particularly thin for comfort and cosmetic reasons. With some patients having high center palates it may not be always possible to completely conform the tray to the palate areas resulting in a small air space during the conforming process and a greater thickness of denture plastic in such areas will result. However, even in such cases a very satisfactory denture is produced. Similarly, undercut and other unusual isolated irregular areas in the gums of the patient are disregarded in the conforming operation and result in areas of greater thickness which are, of course, desirable in a denture.

The spacer may be made from any of several suitable materials and may be pre-formed to adapt to the shaping of the tray or may be a sheet material which can be shaped under mild pressure to take the shape of the tray. When employing a sheet material, it is preferred to employ a material which has satisfactory drape properties so that it will approximately conform to the shape of the tray and gums and palate of the patient without substantial bunching or overlapping, thereby avoiding the production of an untrue conformation in the tray. A sheet material providing satisfactory results is a sheet of pure gum rubber. A suitable spacer having a uniform thickness of about 0.0625 inch may be made simply by cutting an arch-shaped piece from a commercially available sheet of pure gum rubber. Another suitable spacer is similarly made from 0.05 to 0.125 inch thick "Minicel" L-200 cross-linked polyethylene foam. In general, it is now preferred to use a spacer which has been preformed to the shape of the tray and accordingly fits just inside the tray substantially in contact with the inside of the inner and outer walls and palate in the case of an upper denture. A preferred such preformed spacer is readily prepared from the same Boxing Wax which is preferred as the deformable material, and preferably averages about 0.05 to 0.10 inch in thickness. Such a wax spacer may be prepared by joining adjacent strips of wax, by forming as by vacuum forming and the like from wax sheets, or by casting or molding or any other suitable technique. To assist in preventing sticking to the tray and to facilitate separation from the tray, it is preferred to coat the underside or contacting surfaces of the wax spacer with a layer of lacquer, or other suitable material essentially acting as a mold release material with respect to the wax. A preferred such preformed wax spacer 56 for use in forming an upper denture is illustrated in FIG. 6 and a preferred preformed wax spacer 58 of analogous construction for use in forming a lower denture is shown in FIG. 7.

The formable tray 20 or 20a after conforming to the gums and palate of the patient as illustrated, for example, in FIG. 8, results in a conformed tray or former which is then employed to form a denture, desirably by molding in situ in the mouth of the patient according to the preferred aspects of the basic method described in our U.S. Pat. No. 3,621,575 and copending application Ser. No. 126,507. In accordance with such preferred basic method, a first layer of liquid pigmented denture-forming material capable of cold curing to a rigid acrylic polymer is deposited in the tray and distributed over the palate portion and in the gum-receiving portion of the trough over the false teeth. A preformed upper shim, which is complete in the sense of having both a palate portion and gum-receiving portion and composed, for example, of either a single layer or two laminated layers of DYNEL acrylic woven clotch and painted with a pigmented liquid acrylic monomer is painted on its bottom surface with the balance of the rigid denture-forming desired in the first layer to be formed in the tray and then positioned over the rigid denture-forming material previously distributed in the tray. Other suitable shims may be composed of nonwoven polyester cloth (Style 410 of J. P. Stevens Nonwovens, Inc.) and from polyester/acrylic combinations (Nyrel Mod Acrylic Style L 90-1 of the Foss Company) which have been similarly painted and pigmented. The second layer of denture-forming material constituting a liquid pigmented material capable of cold curing to a semi-rigid or semi-hard acrylic polymer is then deposited and distributed over the shim and the resulting assembly inserted into the mouth of the patient and molded in situ to the gums and palate. If desired, the gums and palate of the patient may be lightly coated with a light mineral or other oil or vaseline to reduce the effects of heat of curing. The preferred denture-forming materials are as described in said U.S. Pat. No. 3,621,575 and application Ser. No. 126,507 and the amounts thereof and the volume proportions of lower rigid material to upper semirigid material are preferably the reduced amounts disposed in said Ser. No. 126,507, except that a small amount of a light oil, preferably a natural oil, desirably peppermint oil, may be incorporated into at least the second layer denture-forming materials. Thus, the first layer rigid material may be preferably prepared by adding 3.7 cc. of liquid acrylic monomer to which 3–5 drops of peppermint oil of the pigmented resin powder, both said liquid and powder obtained under the trademark "DURALINER." The second layer semi-rigid material is preferably prepared by adding 6.0 cc. of liquid monomer to which 3–5 drops of peppermint oil may be added to 7.75 gms of the pigmented resin powder, said liquid component obtained as special order component 2-A and said powder component obtained as special order component 3-A, both from the American Consolidated Manufacturing Company of Philadelphia, Pa. The peppermint oil may be any commercially available type and the amount generally of any oil such as peppermint oil may vary from about 1% to 5%, based on the total weight of the liquid monomer component used in forming the denture.

The denture formed in situ in the tray and in the mouth of the patient is removed from the mouth after curing of the denture-forming material which takes typically about 3–10 minutes, one advantage of the oil, e.g. the peppermint oil, being that the cured time is slightly more delayed to permit easier working in the mouth as desired or required to insure proper positioning and squeezing out of excess material. The resulting denture as formed in the tray is illustrated in FIGS. 13 and 14 wherein the conformed tray 60 is shown in dotted line outline. The denture 62 has the shim 64 imbedded therein between the first layer 66 of rigid material and second layer 68 of semi-rigid material, and the conformed tray is readily separated from the denture which may be finished by polishing and the like.

The invention also provides a novel and efficient means and method for preparing the preferred basic trays 21 and 23 by vacuum forming. Heretofore, we had prepared a tray for in situ denture formation by vacuum forming over a one piece die block having the general shape of a set of false teeth and then later inserting or casting a set of false teeth in the cavities or depressed pocket portions thereof. As illustrated in FIGS. 9–12, inclusive, we now employ a die block 70 similar to that previously used except that the teeth are absent and replaced by a teeth holding channel generally designated 72 which preferably constitutes an outline of the bottom of a set of false teeth 74 which can be positioned and held on the die block 70 by the depression, groove or channel 72. A die block 70 for an upper basic tray therefore comprises, as shown particularly in FIGS. 9 and 10, a slightly enlarged replica of the natural gums 76 comprising the teeth holding bottom portions 78, outer gum side 80 and inner gum side 82, and an impressed replica of the palate 84 which is integral with the inner gum side 82. The lower portion of the die block constitutes a base 86 which is sufficiently high to insure good vacuum forming. The gums and palate also contain a plurality of holes 88 which are drilled entirely through the block to insure good vacuum forming. The teeth holding channel 72 has a channel bottom 90 adapted to mate with and support the bottom or route end of the teeth which are preferably slightly concave and accordingly the channel bottom is preferably slightly convex. Hence, the bottom essentially comprises a plurality of contiguous indicia 91 which are preferably convex in shape. The channel at is side which is adjacent the outside gum side 80 terminates at a side wall or ridge line 92 which is preferably continuous although the depth of the side wall or ridge line may be very shallow or virtually non-existent at the points of maximum distance from an imaginary longitudinal center line of the channel, i.e., the points where the center of bottom front edge of the false teeth will rest. The side wall or ridge line 92 preferably increases in depth proceeding away from said points of maximum distance and form a pluraity of protuberances 94 which essentially replicate the portion of natural gums which protrude between natural teeth. The outline of the ridge line therefore essentially corresponds to the outline formed by the front portion of the bottom of the false teeth and can be said to comprise the protuberances 94 and arch-like ridge portions 95 which join the protuberances. In practice, the cast set of false teeth 74 shown in FIG. 12 may be held on the die block 70 solely by the ridge line 92 inasmuch as such ridge line 92 and its protuberances 94 prevent the false teeth from being pushed down off the die block during vacuum forming and the protuberances 94 similarly secure the false teeth against undesired lateral movement. It is therefore not necessary that the side of the channel adjacent the inner side gums terminate in an inner side wall or inner ridge line although the same is preferred as shown in FIG. 9. However, if desired, small pins or pegs (not shown) and 2-4 millimeters in height above the die block may be secured between front teeth in the interproximal region, e.g. between the second bicuspid and first molar on each side, to further provide against movement. In general, the inner ridge line 96, including its protuberances 98, are preferably of shallower depth than the corresponding outer ridge line 92 and its protuberances 94, and again the depth at the points of maximum distance from the imaginary longitudinal center line may be very shallow or non-existent.

The die block 70 is preferably of dentist's stone and may be prepared using conventional techniques from a set of already made dentures by taking a standard impression thereof in a material such as alginate. Prior to taking the impression the outer gums wall of the denture may be built up, cut away, or the like in order to introduce dimensions desired in the final die block. After taking the impression of the denture, it is cast in stone to obtain a stone model of the denture from which the teeth are then removed by cutting, grinding or similar means. The ridge line 92 with its protuberances 94 and optionally the inner ridge line 96 and its protuberances 98 may be introduced in the stone model by cutting with a strong small knife or by equivalent means to form the desired die block. The holes 88 may be drilled through the formed die block by conventional procedures. A die block for a lower tray may be similarly prepared from a set of lower dentures. The shape of the arch of the false teeth and accordingly the trays provided by the invention preferably conform to the anatomical curve. A number of such die blocks of varying size are used to make different sized trays.

The basic tray 21 may be prepared using the die block 70 by first placing thereon a set of false teeth such as the false teeth 74 shown in FIG. 12. The false teeth 74 are appropriately secured in the channel 72 of the die block 70. When preparing the tray from the preferred ethylene/vinyl acetate sheet material of preferred 6 mil thickness, or other sheet material which can be easily deformed because of its nature and/or thinness, it has been found desirable to coat the preferred pre-cast acrylic false teeth with a pressure-sensitive or other non-setting adhesive so that the basic tray material will be removably bonded or secured to the teeth and thereby prevent the flow of denture-forming material over the teeth during the preparation of denture. It is not necessary to coat the entirety of the teeth but at least the surfaces near the gum line are desirably entirely coated with the adhesive. A suitable such adhesive is a cyanoacrylate based adhesive obtained under the trade designation "Eastman 910". The die block 70 with the adhesive coated teeth secured in the channel 72 of the die block is positioned on the suction plate of a conventional vacuum forming machine, a sheet of suitable plastic material 100 placed thereover, and the vacuum former operated to conform under the heat and pressure thereof the sheet 100 to the false teeth holding die block whereby the indica or pockets 40 of the basic tray are formed around the teeth which are adhered thereto by reason of the adhesive, and in general the substance or outline of the basic tray 21 with teeth therein is produced. The false teeth thus comes away from the die block when the sheet material is removed therefrom and the resulting crude basic tray with teeth therein is converted to the basic tray by simply cutting away the excess sheet material. The preferred basic trays do not hold their shape well on their own at this point and are preferably placed on a suitable holding block (not shown) or replaced on the die block and converted to the preferred deformable tray 20 by coating the walls and palate thereof with the deformable material. Application of the deformable material may be accomplished by coating the preferred Boxing Wax on the walls and palate using a hot spatula. In another method, the bottom of the die block or holding block may be readily equipped with a handle (not shown) and the application of the wax achieved by repeated dippings into a bath of molten wax followed by cooling and the removal, as by cutting with a dull knife, of the wax which covers the lower part of channel holding the false teeth. The preferred Boxing Wax has a natural adherence for the ethylene/vinyl acetate sheet material so that the use of an adhesive is not necessary. An additional advantage of forming an upper tray by vacuum forming of a thin, e.g. 6 mil, sheet of the preferred ethylene/vinyl acetate materials is that the sheet portion over the palate is stretched during the vacuum forming to an even thinner sheet having only about 40% to 75% of the thickness of the outer tray wall, and thus, the palate portion of the tray can be further more easily stretched during the conforming step to the limited extent usually desired to conform the same sufficiently to most palate variations.

While it is desirable to form the denture in situ in the mouth of the patient, the conformed tray may be used to form a denture outside the mouth using the stone of impression of the patient's gums by placing the conformed tray and stone impression in an articulator and proceeding to form the denture therein using cold-cure denture forming material.

It will also be evident that various features collectively incorporated into the preferred embodiments of the invention may be used individually or together with other features not involved in this invention to gain advantages in the formation of dentures, and the modifications, if any, in the structures disclosed herein to carry out such variations will readily occur to those skilled in the art. For example, advantages may be gained by employing a tray in which either the inner or outer wall portion are made formable. In an upper tray advantages can be also gained when only the inner wall and palate integral therewith are made formable, and also when only the palate is made formable, particularly when the palate is not only formable but consists essentially of a formable material which is also speadable or stretchable as described herein in connection with the second preferred embodiment hereof. Similarly, an upper tray in which only the outer wall portion is formable may be used in forming a fully adapted or conformed tray or former by taking an impression of only the palate and inner gum side in such a tray using an impression material such as alginate while separating the impression material and gums and palate of the patient with a spacer in accordance with such a modification of the invention disclosed in the application Ser. No. 126,507, it being noted that the spacers disclosed in said application and herein are of similar structure and accomplish essentially the same purpose. In terms of incorporating the formable palate feature of this invention into other structures one may contemplate, for example, another modification leading to a less preferred tray which would be a tray of the type described in our U.S. Pat. No. 3,460,252 in which the palate or a portion of the palate is cut-away and replaced by formable material whereby the advantages of having a palate consisting essentially of formable material may be realized, in which case the spacer contemplated herein need not be a full spacer but one sufficient to cover only the palate or the palate and inner tray walls.

It will also be evident that the various improvements provided by the present invention may be realized in general in the formation of dentures, particularly the in situ formation of dentures involving methods utilizing a device or assembly carrying false teeth and having wall means establishing a gum-receiving portion or trough adapted to hold denture-forming material which is curable at mouth temperatures to take the shape of and fit to a patient's gum, including especially devices or assemblies in which inner and outer removable wall portions form the gum-receiving trough and in which the curable denture-forming material functions to join together the resulting artificial gum and the false teeth.

What is claimed is:

1. A tray which functions as a former for in situ forming a denture comprising a basic tray having inner and outer wall portions defining a trough of which the upper portion thereof defines at least a lower portion of a gum-receiving portion and the lower portion thereof defines an area adapted to hold false teeth, and a formable material adjacent said gum-receiving portion and secured to at least one of said wall portions whereby said formable material and wall portion to which it is secured form a tray wall moveable by said formable material from one position of rest to another position of rest adjacent said gum-receiving portion.

2. A tray assembly in accordance with claim 1 in which false teeth are held in said area adapted to hold false teeth.

3. A tray in accordance with claim 1 in which the inner and outer basic tray wall portions define essentially the entirety of the gum-receiving portion and in which formable material is secured to both said inner and outer wall portions.

4. A tray in accordance with claim 1 in which at least the basic tray wall portion having formable material secured thereto is a flanged wall.

5. A tray in accordance with claim 1 in which the inner and outer basic tray wall portions define a flanged channel and in which formable material is secured to both said inner and outer wall portions.

6. A tray in accordance with claim 2 which functions as a former for a lower denture in which the inner and outer basic tray wall portions define essentially the entirety of the gum-receiving portion and in which formable material is secured to both said inner and outer wall portions.

7. A tray in accordance with claim 2 which functions as a former for a lower denture in which the inner and outer basic tray wall portions define a flanged channel and in which formable material is secured to both said inner and outer wall portions.

8. A tray in accordance with claim 2 which functions as a former for an upper denture in which the inner and outer basic tray wall portions define essentially the entirety of the gum-receiving portion, in which a basic tray palate portion is integral with said inner basic tray wall portion and in which formable material is secured to at least said inner wall portion and to said palate portion whereby said palate portion as well as the resulting inner tray wall may be moved from one position of rest to another position of rest by said formable material.

9. A tray in accordance with claim 8 in which formable material is also secured to the outer wall portion.

10. A tray in accordance with claim 2 which functions as a former for an upper denture in which the inner and outer basic tray wall portions define a flanged channel, in which formable material is secured to at least said inner wall portion and in which a palate portion of formable material is integral with the formable material secured to the inner wall portion whereby said palate portion as well as at least the resulting inner tray wall may be moved from one position of rest to another position of rest.

11. A tray in accordance with claim 10 in which formable material is also secured to the outer wall portion.

12. A tray in accordance with claim 2 in which the false teeth carried in the lower portion of the trough are removably secured by an adhesive material to the basic tray wall portions.

13. A tray in accordance with claim 12 in which the basic tray includes a bottom portion integral with the inner and outer basic tray wall portions.

14. A tray in accordance with claim 2 in which the formable material is a heat deformable material.

15. A tray in accordance with claim 6 in which the basic tray includes a bottom portion integral with the inner and outer basic tray wall portions and in which the formable material is a heat deformable material.

16. A tray in accordance with claim 15 in which the basic tray is composed of thin sheet material of an ethylene/vinyl acetate copolymer comprising 65% to 85% ethylene and 12% to 35% vinyl acetate and having a Vicat softening point not in excess of 160° F., in which the false teeth are removable secured by an adhesive material to the basic tray wall portions adjacent said teeth and in which the heat deformable material is a wax formable at a temperature above 130° F.

17. A tray in accordance with claim 7 in which the basic tray includes a bottom portion integral with the inner and outer basic tray wall portions and in which material is a heat deformable material.

18. A tray in accordance with claim 17 in which the basic tray is composed of thin sheet material of an ethylene/vinyl acetate copolymer comprising 65% to 85% ethylene and 12% to 35% vinyl acetate and having a Vicat softening point not in excess of 160° F., in which the false teeth are removable secured by an adhesive material to the basic tray wall portions adjacent said teeth and in which the heat deformable material is a wax formable at a temperature above 130° F.

19. A tray in accordance with claim 9 in which the basic tray includes a bottom portion integral with the inner and outer basic tray wall portions and in which the formable material is a heat deformable material.

20. A tray in accordance with claim 19 in which the basic tray is composed of thin sheet material of an ethylene/vinyl acetate copolymer comprising 65% to 85% ethylene and 12% to 35% vinyl acetate and having a Vicat softening point not in excess of 160° F., in which the false teeth are removable secured by an adhesive material to the basic tray wall portions adjacent said teeth and in which the heat deformable material is a wax formable at a temperature above 130° F.

21. A tray in accordance with claim 11 in which the basic tray includes a bottom portion integral with the inner and outer basic tray wall portions and in which the formable material is a heat deformable material.

22. A tray in accordance with claim 21 in which the basic tray is composed of thin sheet material of an ethylene/vinyl acetate copolymer comprising 65% to 85% ethylene and 12% to 35% vinyl acetate and having a Vicat softening point not in excess of 160° F., in which the false teeth are removable secured by an adhesive material to the basic tray wall portions adjacent said teeth and in which the heat deformable material is a wax formable at a temperature from 130° F.

23. In a walled tray for forming a denture in situ in the tray by molding of curable denture-forming material in contact with the gums of a patient or a model of the gums of a patient, said tray comprising false teeth and having uprising inner and outer walls defining with the top of the false teeth a gum-receiving portion; the improvement in which at least one of said walls comprising a formable material secured to the outside of a corresponding wall portion of non-formable material whereby the resulting wall comprising said wall portion with formable material secured thereto may be removed by said formable material from one rest position to another position of rest adjacent said gum-receiving portion.

24. A tray in accordance with claim 23 for forming a lower denture in which both said inner and outer walls comprise a formable material secured to corresponding inner and outer wall portions adjacent said gum-receiving portion whereby the resulting walls comprising formable material and inner and outer wall portions may be moved by said formable material from one rest position to another position of rest.

25. A tray in accordance with claim 24 in which the formable material is a heat deformable material.

26. A tray in accordance with claim 23 for forming an upper denture in which the tray includes a palate portion integral with the inner wall, in which at least the inner wall comprises formable material secured to the corresponding inner wall portion adjacent said gum-receiving portion and in which said palate portion comprises formable material whereby said palate portion may be also moved by said formable material from one rest position to another rest position.

27. A tray in accordance with claim 26 in which said outer wall comprises formable material secured to the outside of a non-formable outer wall portion adjacent said gum-receiving portion and in which the formable material is a heat deformable material.

28. In a tray for forming an upper denture in-situ in the tray by molding of a curable denture-forming material in contact with the gums of a patient or a model of the gums of a patient, said assembly comprising false teeth, uprising inner and outer walls defining with the top of the false teeth a gum-receiving portion, and a palate, at least a portion of said walls being of non-formable material; the improvement in which at least a portion of the palate consists essentially of a formable material whereby said palate portion may be removed by said formable material from one rest position to another rest position.

29. A tray in accordance with claim 28 in which the formable material is a heat deformable material.

30. A tray in accordance with claim 22 in which said sheet material has a stiffness not in excess of 9,000 p.s.i.

31. In a method of forming a denture in situ in a tray comprising providing a tray carrying false teeth and having uprising inner and outer walls forming with the false teeth a gum-receiving portion, disposing curable denture-forming material in at least said gum-receiving portion and molding said denture-forming material in contact with the gums of a patient or a model of the gums of a patient; the improvement comprising providing a formable tray in which at least one of said inner and outer walls is formable, disposing said formable tray over the gums of a patient or a model of the gums of the patient while said tray and gums are separated by a spacer having a thickness corresponding to the minimum thickness desired in the denture adjacent such formable wall at both occurrences, and conforming said formable tray to said gums with the spacer therebetween to provide a conformed tray in which the formable portion replicates the corresponding wall at both occurrences of the gums and differs spatially therefrom by the thickness of the spacer.

32. A method in accordance with claim 31 in which the formable portions are heat deformable.

33. A method in accordance with claim 31 in which a lower conformed tray is formed and in which both the inner and outer walls of the formable tray are formable.

34. A method in accordance with claim 31 in which the inner and outer formable walls comprise plastic sheet material and a formable material secured to the outside of said sheet material.

35. A method in accordance with claim 33 in which at least a portion of the inner and outer walls adjacent the upper portion of the gum-receiving portion consist essentially of formable material.

36. A method in accordance with claim 33 in which the formable portions are heat deformable.

37. A method in accordance with claim 35 in which the formable portions are heat deformable.

38. A method in accordance with claim 34 in which the sheet material is a polymeric material having a Vicat softening point not in excess of 160° F. and a stiffness not in excess of 9,000 p.s.i.

39. A method in accordance with claim 31 in which an upper tray is formed and in which the tray includes a palate portion integral with the inner wall.

40. A method in accordance with claim 39 in which the inner wall and palate portion are formable.

41. A method in accordance with claim 39 in which the outer wall is formable.

42. A method in accordance with claim 39 in which the inner and outer walls and palate portion are formable.

43. A method in accordance with claim 42 in which the inner and outer formable walls and formable palate portion comprise plastic sheet material and a formable material secured to the outside of said sheet material.

44. A method in accordance with claim 42 in which the formable portions are heat deformable.

45. A method in accordance with claim 39 in which the inner and outer walls and palate portion are formable, and in which at least a portion of said palate portion consists essentially of formable material.

46. A method in accordance with claim 39 in which at least a portion of the inner and outer walls adjacent the upper portion of the gum-receiving portion and essentially the entirety of the palate portion consist essentially of formable material.

47. A method in accordance with claim 45 in which the formable portions are heat deformable.

48. A method in accordance with claim 46 in which the formable portions are heat deformable.

49. In a method of forming an upper denture in situ in a tray comprising providing a tray carrying false teeth and having uprising inner and outer walls forming with the false teeth a gum-receiving portion and a palate, disposing curable denture-forming material in at least said gum-receiving portion and molding said denture-forming material in contact with the gums of a patient or a model of the gums of a patient; the improvement comprising providing a tray in which at least a portion of said palate is formable, disposing said tray over the gums of a patient or a model of the gums of the patient while said tray and palate of the patient are separated by a spacer having a thickness corresponding to the minimum thickness desired in a denture adjacent such formable palate portion, and conforming such formable palate portion to the patient's palate with the spacer therebetween to provide a conformed tray in which the formable palate portion replicates the corresponding palate of the patient and differs spatially therefrom by the thickness of the spacer.

50. A method in accordance with claim 49 in which the formable portion is heat deformable.

51. A method in accordance with claim 49 in which said formable palate portion consists essentially of formable material.

52. A tray in accordance with claim 10 in which the formable material is a spreadable heat deformable material.

53. A tray in accordance with claim 21 in which the heat deformable material is a spreadable heat deformable material.

54. A tray in accordance with claim 26 in which the formable material is a spreadable heat deformable material.

55. A tray in accordance with claim 27 in which the heat deformable material is a spreadable heat deformable material.

56. A tray in accordance with claim 29 in which the heat deformable material is a spreadable heat deformable material.

57. A method in accordance with claim 32 in which the heat deformable material is a spreadable heat deformable material.

58. A method in accordance with claim 45 in which the formable material is a spreadable heat deformable material.

59. A method in accordance with claim 50 in which the heat deformable material is a spreadable heat deformable material.

60. In a walled tray for forming a denture in-situ in the tray by molding of curable denture-forming material in contact with the gums of a patient or a model of the gums of a patient, said tray comprising false teeth and having uprising inner and outer walls defining with the top of the false teeth a gum-receiving portion; the improvement in which at least one of said walls comprises a formable material and said false teeth being formed of a material different from said formable material, the resulting formable wall being movable by reason of said formable material from one rest position to another position of rest adjacent said gum-receiving portion.

61. A tray in accordance with claim 60 in which the formable material is a heat deformable material.

62. A tray in accordance with claim 61 in which the heat deformable material is a spreadable heat deformable material.

63. In a tray for forming an upper denture in-situ in the tray by molding of a curable denture-forming material in contact with the gums of a patient or a model of the gums of a patient, said tray comprising false teeth, uprising inner and outer walls defining with the top of the false teeth a gum-receiving portion, and a palate; the improvement in which at least a portion of the palate consists essentially of a formable material, said teeth being formed of a material different from said formable material, said palate portion being movable by said formable material from one rest position to another rest position.

64. A tray in accordance with claim 63 in which the formable material is a heat deformable material.

65. A tray in accordance with claim 64 in which the heat deformable material is a spreadable heat deformable material.

66. A tray which functions as a former for use in forming a denture in situ, said tray assembly comprising
   a basic tray having inner and outer flexible walls and
   a flexible walled trough connecting said inner and outer walls, said walls at their upper portion defining a gum-receiving portion and to hold a set of false teeth in proper relationship to each other at the lower portion thereof, a layer of formable material intimately secured to said flexible walls on the sides thereof away from the gum-receiving portion to form a movable tray wall, said formable material being formable under sufficient force and capable of retaining said formed shape whereby said movable tray wall may be shaped from a first position of rest to a second position of rest adjacent said gum-receiving portions.

67. A tray according to claim 66 in which said formable material is formable at elevated temperatures above 130° F.

68. A kit for forming a denture comprising a formable tray having a gum-receiving portion which approximates the shape of the patient's gums, a deformable spacer sheet, a shim and denture-forming materials, said formable tray having inner and outer walls, a trough between said walls defining therewith said gum-receiving portion, a plurality of artificial teeth supported in said gum-receiving portion, said walls including formable material whereby the formable walls are movable from one rest position to another rest position.

69. A kit in accordance with claim 68 wherein said formable tray includes a palate portion, said palate portion including formable material whereby said palate portion is movable from one rest position to another rest position.

70. An assemble for forming a denture in the mouth of a dental patient comprising a tray having inner and outer walls made of formable material and approximating the shape of the patient's gums, a trough between said walls defining therewith a gum-receiving portion, a substantially U-shaped continuous slot formed in the bottom of said trough, said assembly further including a preformed unitary structure including pre-arranged individual artificial teeth and means for removable mounting said teeth in the slot of said formable tray, said removable means comprising an abbreviated basic tray, the bottom portion of which is removed forming a slot in said basic tray, thereby exposing the bottoms of the false teeth.

71. The assembly in accordance with claim 67 wherein said inner walls are connected by said formable material to form a palate whereby the tray is suitable for use in forming a denture for the upper portion of the mouth.

72. The assembly in accordance with claim 67 wherein said formable material is dental baseplate wax.

73. A method of forming an artificial denture for the mouth of a dental patient employing a tray having a gum-receiving portion with a U-shaped continuous slot formed therein, and a preformed unitary structure comprising an abbreviated basic tray, the bottom portion of which is removed forming a slot in said basic tray, thereby exposing the bottoms of the false teeth, the method comprising:

placing a deformable sheet as a spacer over said tray,
a applying pressure to said tray having said spacer therein to conform said tray to the gums of a patient with the spacer between the surfaces of said tray and of said gums,
removing said tray from said gums,
applying a suitable amount of dental acrylic resin to said tray,
placing said tray in contact with said gums with said dental acrylic resin adjacent said gum surfaces,
simultaneously forcing said tray against said gums while allowing said dental acrylic resin to harden,
removing said tray from said gums, and
separating said tray from said hardened acrylic resin whereby said preformed unitary structure and said hardened acrylic resin form a unitary denture.

74. The method of claim 70 further including the step of fitting a shim into said tray in contact with said dental acrylic resin prior to placing said tray in contact with said gums or model.

75. The method of claim 71 wherein said shim is formed of woven acrylic fibers, and wherein said step of fitting said shim into said tray additionally comprises the step of soaking said shim in a solution of acrylic monomer.

76. The method of claim 72 wherein said step of applying a suitable amount of dental acrylic resin into said tray includes the steps of disposing in said tray a first layer of dental acrylic resin, then disposing in contact therewith a shim having a first surface and an opposite surface with said first surface in wetting contact with said first layer, and then disposing a second layer of dental acrylic resin in contact with said opposite shim surface.

* * * * *